United States Patent
Yadav et al.

(10) Patent No.: US 10,329,223 B2
(45) Date of Patent: Jun. 25, 2019

(54) PROCESS FOR PROPYLENE AND LPG RECOVERY IN FCC FUEL GAS

(71) Applicant: RELIANCE INDUSTRIES LIMITED, Mumbai (IN)

(72) Inventors: Manoj Yadav, Haryana (IN); Asit Kumar Das, Gujarat (IN); Sukumar Mandal, Haryana (IN); Amitkumar Parekh, Gujarat (IN); Nilamkumar Limbasiya, Gujarat (IN)

(73) Assignee: RELIANCE INDUSTRIES LIMITED, Maharashtra (IN)

( * ) Notice: Subject to any disclaimer, the term of this patent is extended or adjusted under 35 U.S.C. 154(b) by 64 days.

(21) Appl. No.: 15/187,005

(22) Filed: Jun. 20, 2016

(65) Prior Publication Data

US 2016/0368841 A1 Dec. 22, 2016

(30) Foreign Application Priority Data

Jun. 19, 2015 (IN) .......................... 2347/MUM/2015

(51) Int. Cl.
| | |
|---|---|
| *C07C 7/04* | (2006.01) |
| *C07C 7/09* | (2006.01) |
| *C07C 7/11* | (2006.01) |
| *C10L 3/12* | (2006.01) |
| *C10G 11/18* | (2006.01) |

(Continued)

(52) U.S. Cl.
CPC ............... *C07C 7/005* (2013.01); *C07C 7/04* (2013.01); *C07C 7/09* (2013.01); *C07C 7/11* (2013.01); *C10G 11/18* (2013.01); *C10G 70/041* (2013.01); *C10G 70/043* (2013.01); *C10G 70/048* (2013.01); *C10G 70/06* (2013.01); *C10L 3/12* (2013.01); *C10G 2300/104* (2013.01); *C10G 2400/20* (2013.01); *C10G 2400/28* (2013.01); *C10L 2290/06* (2013.01);

(Continued)

(58) Field of Classification Search
CPC .. C07C 7/005; C07C 7/04; C07C 7/09; C07C 7/11; C10L 3/12; C10L 2290/06; C10L 2290/541; C10L 2290/543; C10G 11/18
See application file for complete search history.

(56) References Cited

U.S. PATENT DOCUMENTS

| | | | |
|---|---|---|---|
| 3,893,905 | A | 7/1975 | Fenske et al. |
| 5,846,403 | A | 12/1998 | Swan et al. |

(Continued)

FOREIGN PATENT DOCUMENTS

| | | |
|---|---|---|
| EP | 0 142 900 A2 | 5/1985 |
| WO | 00/31214 A2 | 6/2000 |

OTHER PUBLICATIONS

Oil & Gas Journal 101, Feb. 10, 2003, 52-53, 56-58.

*Primary Examiner* — Youngsul Jeong
(74) *Attorney, Agent, or Firm* — Ladas & Parry LLP

(57) ABSTRACT

The present invention provides a process for recovery of propylene and LPG from the fuel gas produced in FCC unit by contacting a heavier hydrocarbon feed with FCC catalyst. The process provides an energy efficient configuration for revamping an existing unit constrained on wet gas compressor capacity or for designing a new gas concentration unit to recover propylene and LPG recovery beyond 97 mole %. The process of the present invention provides an increase propylene and LPG recovery without loading wet gas compressor with marginal increase in liquid loads.

10 Claims, 3 Drawing Sheets

Figure 1:
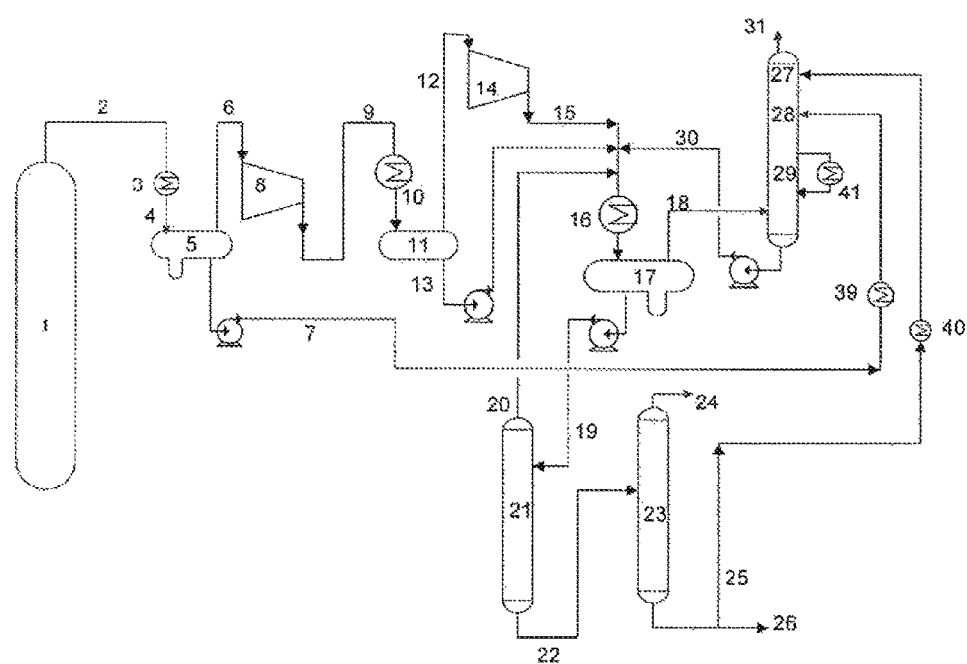

(51) Int. Cl.
    *C07C 7/00*         (2006.01)
    *C10G 70/04*       (2006.01)
    *C10G 70/06*       (2006.01)

(52) U.S. Cl.
    CPC ..... *C10L 2290/30* (2013.01); *C10L 2290/541* (2013.01); *C10L 2290/543* (2013.01)

(56) References Cited

U.S. PATENT DOCUMENTS

| | | |
|---|---|---|
| 7,074,323 B2 | 7/2006 | Ghijsen |
| 8,618,344 B2 * | 12/2013 | Yadav .................... C10G 11/18 208/347 |
| 2002/0003103 A1 | 1/2002 | Henry et al. |

* cited by examiner

PROCESS FOR PROPYLENE AND LPG RECOVERY IN FCC FUEL GAS

FIELD OF INVENTION

Present invention provides process for the enhanced recovery of propylene and LPG from the fluid catalytic cracking (FCC) fuel gas, a product separated from a mixture of hydrocarbons produced by contacting a heavier hydrocarbon feed with FCC catalyst. The invention relates to a process for recovery of propylene without loading wet gas compressor and without requiring any additional fractionation column.

BACKGROUND OF INVENTION

Fluid catalytic cracking (FCC) is one of the most important conversion processes used in petroleum refineries. It is widely used to convert the high-boiling, high-molecular weight hydrocarbon fractions of petroleum crude oils to more valuable gasoline, olefinic gases, and other products. FCC is a vital unit in refinery operations due to its impact on overall refinery profitability. Due to its importance, operation of the FCC is shifting to meet changing market demands for particular fuel specifications, such as to maximize particular products, such as diesel fuel, LPG, propylene etc.

In the conventional process of propylene and LPG recovery from FCC main column overhead product mixture, the gaseous fraction from the main fractionator condenser/separator is fed to a two stage compressor. The first stage discharge is partially condensed and cooled in inter-stage coolers. The resulting liquid and gaseous fractions are separated in inter-stage receiver. Second stage compressor discharge after combining with the liquid fraction from first-stage receiver is condensed and cooled in second stage high pressure condenser/coolers and received in a high pressure receiver cum separator.

The liquid fraction from high pressure receiver is fed to a de-ethanizer column or $C_2$- stripper where ethane, ethylene and lighter material present in the feed are removed. The overhead vapours from stripper are recycled back to high pressure receiver via high pressure coolers. Bottom product of the stripper is fed to a debutanizer column where propylene is obtained as a part of the overhead product and the bottoms product thus obtained is referred to as stabilized naphtha.

The gaseous fraction from high pressure receiver is supplied to an absorber. In the absorber, $C_3$-$C_4$ components present in the gaseous feed are preferentially absorbed by an absorber fluid also referred to as absorber oil or lean oil. Overhead liquid from the main fractionator (typically known as unstable naphtha) and debut bottoms liquid (typically known as stabilized naphtha) are commonly used as absorber oil. Typical temperature of lean oil supplied to the absorber column is between 30 and 40° C. Side coolers are provided to remove heat of absorption from absorber oil. Rich absorber oil from absorber bottom is cooled and supplied to high pressure receiver from where it is fed to de-ethanizer column. Absorber overhead gases are further treated to recover any gasoline range material still present in the gas leaving the absorber.

Due to the presence of significant quantity (>5 mol %) of propylene present in the unstabilized naphtha stream, the recovery of propylene is limited up to 97% in the conventional process. Presence of significant quantity (>5 mol %) of propylene in the unstabilized naphtha stream results in significant reduction in mass transfer of propylene from fuel gas to absorber oil.

WO2000031214A2 describes a process for the recovery of an olefin from a gas feed stream comprising hydrocarbons and minor amounts of olefins. The process comprises introducing the gas feed stream into a single recovery distillation column; withdrawing an overhead vapor stream from said column; cooling and partially condensing the overhead vapor stream in the overhead condenser; phase-separating the overhead vapor-liquid in the reflux drum; withdrawing from the reflux drum, an olefin-lean, overhead vapor stream and recycling the separated liquid from the reflux drum to the column; withdrawing from the column, a liquid $C_3$+, $C_4$+, $C_5$+, or $C_6$+ bottoms product stream; recycling a portion of the liquid bottoms product stream to the overhead condenser or the upper tray section of said column; and withdrawing an olefin-rich, vapor phase, side product stream rich in a selected olefin.

U.S. Pat. No. 7,074,323 B2 describes a process to debottleneck the conventional process for gas concentration unit wherein unstabilized naphtha, a liquid fraction obtained by cooling the main fractionator overheads and subsequently separating the obtained gaseous and liquid fractions, is separated by distillation into a heavy boiling fraction (initial boiling point 100-160° C.) and a lighter fraction (final boiling point 10-160° C.). The lighter fraction after being cooled between 8 to about 25° C. is fed to the absorber while the heavier fraction is directly fed to the debutanizer. This reduces liquid and gas loads on absorber, stripper and debutanizer. However, the recovery of propylene is not much improved since the lighter fraction contains in fact higher percentage of propylene than the original cut before fractionation. Besides this the main objective of U.S. Pat. No. 7,074,323 B2 is to reduce the load on $C_2$ stripper and debutanizer section rather than improving propylene recovery.

U.S. Pat. No. 3,893,905 describes a process wherein a hydrocarbon feed contacts cracking catalyst at cracking conditions in a reaction zone, reaction products are withdrawn from the reaction zone and introduced into a fractionation zone, overhead vapors from the fractionation zone are passed to a condenser, and effluent from the condenser passes in separate conduits to gas concentration facilities, the improvement comprises: condensing overhead vapors in a differential condenser and in the differential condenser separating overhead vapor into a gaseous phase containing propylene and a liquid phase comprising hydrocarbon molecules having four or more carbon atoms, separation is effected by withdrawing liquid phase upon condensation to form gaseous and liquid phases containing a non-equilibrium distribution of propylene.

Although recycling of downstream naphtha or a heavier hydrocarbon fraction of FCC has been to an upstream section in U.S. Pat. No. 5,846,403 and incorporation of extra columns for further treating the naphtha is disclosed in US20020003103A1; EP142900A2; U.S. Pat. No. 5,846,403; Oil & Gas Journal 101, 52-53, 56-58, 2003. The extra column(s) for treating the (recycled) naphtha is found to be a reactor column for further cracking of the naphtha in order to increase the propylene yield, and not for increasing propylene recovery in the gas concentration section by stripping the naphtha in the extra column.

The concept of increasing absorptive capacity of naphtha or heavier condensate stream from the main reactor for $C_3$, $C_4$ in the gas concentration section by cooling of the heavier condensate to a deep sub-zero temperature is disclosed in WO2000031214A2. Besides this, the concept of pre-empting mixing of $C_3$, $C_4$ with the heavier condensate after the main reactor by incorporating differential condenser is disclosed in U.S. Pat. No. 3,893,905.

As already mentioned in the conventional process, the product mixture from FCC main column overhead comprising naphtha, LPG and fuel gas, are first condensed and gravity separated to produce unstabilized naphtha, which is subsequently used, along with debutanizer naphtha, to absorb propylene and LPG from fuel gas. One of the approaches to enhance propylene recovery beyond 97% is by recycling more of debutanized bottoms viz., stabilized naphtha in combination with the unstabilized naphtha to the absorber. This approach, after a limited success within the design limits, ultimately hits vapor-liquid flooding or reboiler/cooling duty limits in any of the C2 stripper, debutanizer and the absorber column. This requires providing higher gas-liquid capacities and reboiler duties in new designs or by debottlenecking the existing the absorber, de-ethanizer or debutanizer columns constrained due to vapor/liquid flooding or due to limited reboiling duties. Thus, disproportionately large column capacity and reboiler duties need to be provided in the new designs or through revamp of existing units in this approach.

Another approach as followed in the process disclosed in Indian Patent Application No. 1570/MUM/2009 achieves this objective by supplying lean absorber oil generated by stripping off $C_4$ and lighter components from unstabilized naphtha in a separate column. Though this process improves propylene and LPG recovery with no additional recycle of debutanizer naphtha, it requires additional compression capacity, condensers capacity and reboiler duty for recycling the stripped off lighters.

Still another approach is to minimize or completely withdraw the unsaturated naphtha from the primary absorber since unsaturated naphtha is substantially rich in propylene and LPG content and to supply only the debutanizer naphtha at higher flows to the absorber to enhance absorption of propylene. The unsaturated naphtha is directly fed to high pressure receiver or $C_2$ Stripper; additional capacity and associated reboiler duties for each of the existing de-ethanizer and debutanizer needs to be provided in this case to accommodate increased gas-liquid flows, though no additional column for fractionation is required. No additional wet gas compression capacity is required.

The processes possible for achieving same improvement in propylene and LPG recovery are summarized below:
1. Debottleneck/design to provide additional capacity for each of the absorber, de-ethanizer and debutanizer to accommodate increased gas-liquid capacities and associated reboiler duties for increasing recycle flow of Debutanizer naphtha (along with unsaturated naphtha) to the Primary Absorber.
2. Providing an additional column and reboiler duty for stripping the lighters from unstabilized naphtha to supply additional lean absorber oil (along with the debutanizer naphtha) to primary absorber. The stripped off lighters which are cooled and recycled back requiring additional wet gas compressor capacity.
3. Feeding the unsaturated naphtha directly to high pressure receiver or $C_2$ stripper bypassing the absorber as disclosed in the present invention. Only debutanizer naphtha at higher flows is supplied to the absorber; additional capacity and associated reboiler duties for each of the de-ethanizer and debutanizer needs to be provided in revamp/new design to accommodate increased gas-liquid flows. However, no additional column for fractionation or no additional wet gas compression is required.

The process configuration as disclosed in prior art requires minimum energy and minimum tray area but requires additional wet gas compressor capacity. For the wet gas compressor constrained units, the process disclosed in the present invention is efficient in terms of energy and total distillation area requirements for enhancing the recovery of propylene and LPG from fuel gas beyond 97 wt %.

OBJECTS OF THE INVENTION

The main object of the present invention is to develop a process for recovery of propylene and LPG from FCC fuel gas which avoids inconvenient and/or expensive hardware like turbo compressor and condensers or differential condensers.

Another important object of the present invention is to provide a process which makes available higher amount of stabilized naphtha to the gas concentration section, thereby demonstrating higher process convenience and profit-worthiness.

Still another object of the present invention is to provide an energy efficient process for revamping/designing a unit limited by wet gas compressor capacity for enhancing the recovery of propylene and C4s from a product mixture obtained by contacting a hydrocarbon feed with a catalyst in a FCC process.

Further object of the present invention is to develop a process which avoids cooling the unstabilized naphtha to deep sub-ambient temperatures and absorb more $C_3$, $C_4$ in the gas concentration section and helps in keeping sulfides lower in the propylene.

Yet another object of the present invention is to provide a process for more than mole 97% recovery of propylene and LPG from FCC fuel gas.

Still another object of the present invention is to provide a process for recovery of propylene and LPG from FCC fuel gas without loading wet gas compressor.

SUMMARY OF THE INVENTION

The present invention provides a process for enhancing recovery of gaseous products from the product mixture obtained by contacting a hydrocarbon feed with a catalyst in a fluid catalytic process. The present invention provides a process which recovers propylene and C4s in an absorber using, as lean oil, a liquid fraction obtained by condensing main fractionator overhead vapors into gas—liquid fractions followed by separation into gas and liquid fractions. As absorber oil, this liquid fraction has its capacity limited due to significant amounts of propylene and C4s absorbed in it during its formation in main column overhead condenser. In the present invention, this liquid fraction is not used directly as lean oil in the Absorber; instead this liquid fraction is first made completely free from dissolved C3-C4 hydrocarbons by sequentially processing it in the existing De-ethanizer and Debutanizer columns and then used as lean oil in higher amounts to absorb higher amounts of propylene and C4s in the absorber.

The energy efficient process of the present invention comprises the following sequence of steps:
(i) distilling the product mixture obtained by contacting a hydrocarbon feed with a catalyst in a FCC process in main fractionator to obtain heavier liquid products as side/bottom draws and a gaseous top product consisting of components boiling below 215° C.;

(ii) cooling and condensation of the gaseous top product followed by separation of the obtained gas-liquid mixture in a receiver cum separator to obtain a liquid fraction referred to as 'Unstabilized naphtha' and a lighter gaseous fraction;

(iii) sequentially compressing, cooling and separating in a two stage Wet Gas compressor train said gaseous fraction obtained from step (ii) to obtain gaseous and liquid fractions from a high pressure separator;

(iv) mixing the liquid fraction as obtained in step (ii) with the liquid fraction as obtained in step (iii) in high pressure separator to obtain combined liquid fraction;

(v) feeding the combined liquid fraction as obtained in step (iv) to a de-ethanizer column wherein ethane and lighter components stripped off from the feed are recycled back to high pressure receiver in step (iii) whereas the de-ethanized liquid product is fed to debutanizer column;

(vi) separating butane and lighter components present in the debutanizer feed as overhead gaseous fraction and obtaining heavier fraction as bottom product referred to as debutanizer bottoms;

(vii) contacting gaseous fraction obtained from high pressure separator in step (iii) in an absorber with a part of the debutanizer bottoms viz., a part of the liquid fraction as obtained in step (vi);

(viii) feeding the rich oil from the absorber bottom liquid to de-ethanizer via high pressure receiver;

(ix) optionally further treating the gaseous fraction from the absorber before leaving the FCC gas concentration section as fuel gas;

characterized by feeding the entire or a part of unstabilized naphtha as obtained in step (ii), to the de-ethanizer via high pressure receiver and contacting the a part of debutanizer naphtha as obtained in step (vi) with the gaseous fractions obtained from high pressure separator in step (iii) in an absorber.

In an embodiment of the present invention the main fractionator overhead condenser pressure is from 10 psig and above, preferably 25 psig and above.

In yet another embodiment of the present invention the debutanized naphtha is supplied to the absorber at temperature preferably between from about 20° C. to about 30° C. using chilled water/cooling water as an indirect cooling media.

BRIEF DESCRIPTION OF THE ACCOMPANYING DRAWINGS

The present invention is described with reference to the accompanying drawings which:

FIG. 1: Illustrates the prior art/conventional process of recovery of propylene and LPG.

Figure 2:
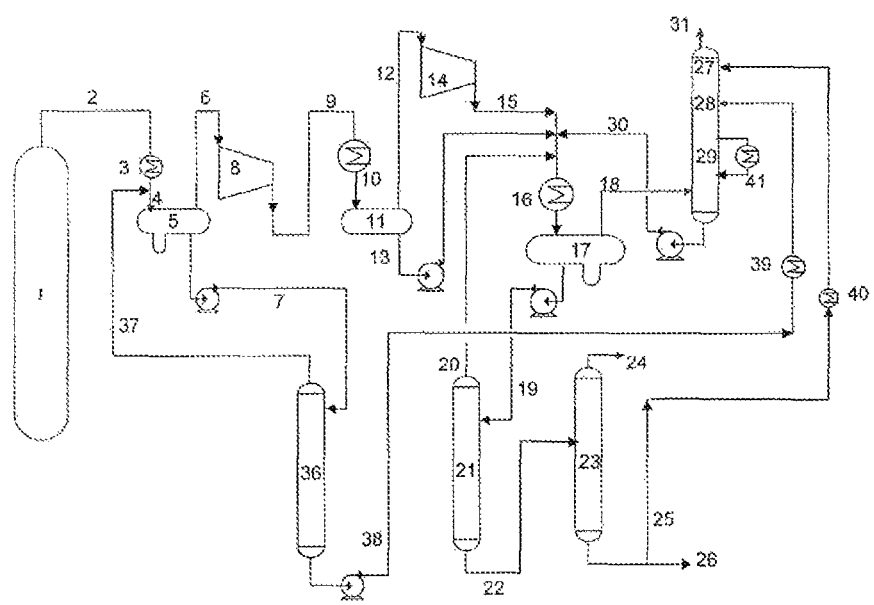

FIG. 2: Illustrates the prior art process of recovery of propylene and LPG from the fuel gas produced in FCC unit.

Figure 3:
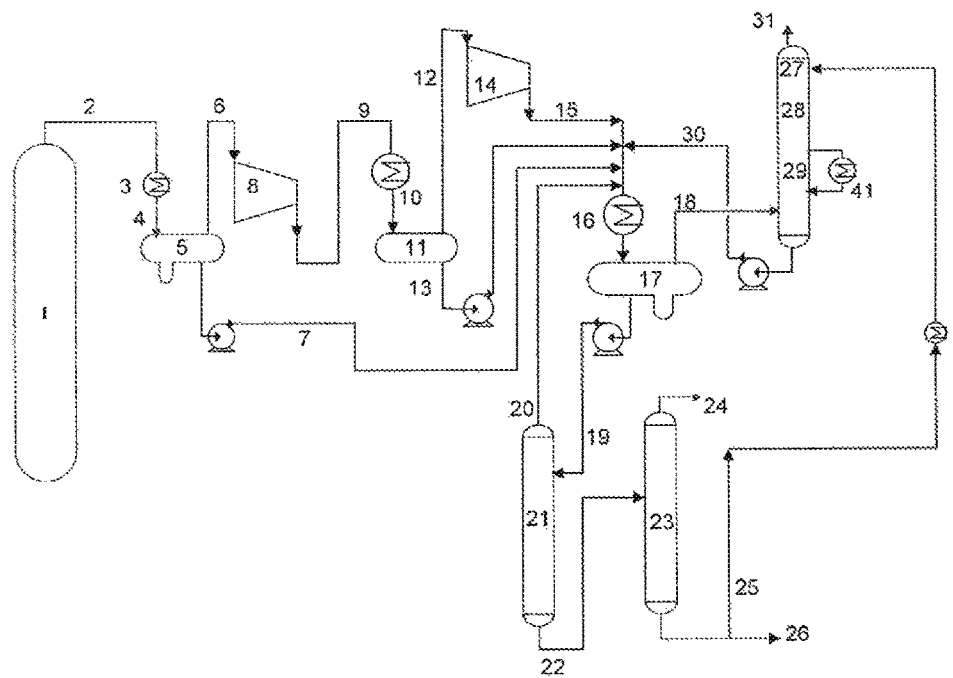

FIG. 3: Illustrates the process of recovery of propylene and LPG from the fuel gas produced in FCC unit as disclosed in the present invention.

DETAILED DESCRIPTION OF THE INVENTION

The present invention provides a process for enhancing recovery of propylene and LPG from the fuel gas produced along with other hydrocarbon products like LPG, naphtha and slurry oil in FCC unit by contacting a heavier hydrocarbon feed with FCC catalyst. The process provides an efficient configuration for revamping an existing unit constrained on wet gas compressor capacity or for designing a new gas concentration unit to recover propylene and LPG recovery beyond 97 mole %. In the conventional process, the product mixture from FCC main column overhead comprising naphtha, LPG and fuel gas, are first condensed and gravity separated to produce unstabilized naphtha, which is subsequently used, along with debutanizer naphtha, to absorb propylene and LPG from fuel gas. For achieving recoveries beyond 97% by increasing recycle of the debutanizer naphtha to the absorber, disproportionately large column capacity and reboiler duties need to be provided in the new designs or through revamp of existing units. The process configuration as disclosed in prior art, achieves the same objective by supplying lean absorber oil generated by stripping off $C_4$ and lighter components from unstabilized naphtha in an additional separation column. Though the above disclosed process improves propylene and LPG recovery with no additional recycle of debutanizer naphtha, it requires additional compression capacity for recycling the stripped off lighters.

The process of the present invention achieves recovery of propylene and LPG from FCC fuel gas by effectively utilizing the additional capacities of primary absorber, $C_2$ stripper and debutanizer columns without loading wet gas compressor capacity.

The process of the present invention provides an efficient process to increase propylene and LPG recovery without loading wet gas compressor with marginal increase in liquid loads.

The key to the process of the present invention is to minimize or completely withdraw the unsaturated naphtha from the primary absorber since unsaturated naphtha is substantially rich in propylene and LPG content and to supply only the Debutanizer naphtha (free of propylene and LPG) at higher flows to the absorber to enhance absorption of propylene.

In the present invention the unsaturated naphtha is directly fed to high pressure receiver or $C_2$ stripper. Additional capacity and associated reboiler duties for each of the de-ethanizer and debutanizer needs to be provided in revamp/new design to accommodate increased gas-liquid flows. No additional wet gas compression is required in the present invention.

The present invention achieves recovery of gaseous products from the product mixture obtained by contacting a hydrocarbon feed with a catalyst in a FCC process. Specifically, it improves a process which recovers propylene and C4s in an absorber using, as lean oil, a liquid fraction obtained by condensing main fractionator overhead vapors into gas—liquid fractions followed by separation into gas and liquid fractions. As absorber oil, this liquid fraction has its capacity limited due to significant amounts of propylene and C4s absorbed in it during its formation in main column overhead condenser. In the improved process, this liquid fraction is not used directly as lean oil in the Absorber; instead this liquid fraction is first made completely free from dissolved C3-C4 hydrocarbons by sequentially processing it in the existing De-ethanizer and Debutanizer columns and then used as lean oil in higher amounts to absorb higher amounts of propylene and C4s in the absorber.

Higher amounts of propylene and LPG are absorbed by replacing the unstabilized naphtha with much lower flow of debutanized naphtha in the present process. The present invention provides a process for removing C3-C4 hydrocarbons from unstabilized naphtha directly in the existing De-ethanizer and Debutanizer columns before using it as lean oil for absorbing propylene; the lighter C3-C4 hydrocarbons get dissolved in naphtha during condensation of overhead vapors in main fractionator condensers. This debutanized naphtha requires cooling only to ambient temperatures for absorbing C3, C4 from fuel gas in the gas concentration section, thereby avoiding turbo-cooling and necessary extra hardware requirement.

The prior art/conventional process of recovery of propylene and LPG is shown in FIG. 1. Gaseous mixture from top of main fractionator 1 is supplied to overhead cooler-condenser 3 via gas conduit 2, gas-liquid fractions thus obtained are separated in overhead receiver cum separator 5. The separated liquid fraction referred to as unstabilized naphtha is supplied as lean oil in absorber section 28 via liquid conduit 7 after cooling to about 30 to 40° C. in heat exchanger 39. The gaseous fraction is led through conduit 6 to suction of the first stage compressor 8, the discharge stream after getting cooled in inter-stage cooler 10 being separated into gas and liquid fractions in inter-stage receiver 11. This inter-stage liquid fraction, via conduit 13, is combined in conduit 15 with the gaseous fraction compressed in second stage. The combined stream in conduit 15 is further joined by rich oil stream from absorber bottom section 29 via conduit 30 and the overhead gaseous fraction from stripper 21 via conduit 20. The resultant stream is cooled in high pressure cooler 16 and thereafter separated into gas and liquid fractions in high pressure receiver cum separator 17.

The liquid fraction obtained from separator 17 is fed via conduit 19 to a stripper 21 wherein components lighter than ethane are stripped off from the feed and are recycled back to high pressure separator 17 via a sequence consisting of conduit 20, conduit 15 and heat exchanger 16. Bottoms of stripper 21 are fed via conduit 22 to a debutanizer column 23 where components lighter than butane present in the feed are separated as column overheads and are fed further to a propylene separation unit via conduit 24. Part of the debutanizer bottom product, also referred to as stabilized naphtha or debutanized liquid, is cooled to about 30° C. to 40° C. in a heat removal circuit 39 and recycled as lean oil to absorber top section 27 via conduit 25.

Gaseous fraction from the high pressure separator 17, comprising of lighters and $C_3$-$C_5$ components, is fed via conduit 18 to the bottom of absorber wherein $C_3$-$C_5$ components are absorbed by the down-flowing lean absorber oil. Cool stabilized naphtha, being leaner oil than the unstabilized naphtha, is supplied to the top section 27 of the absorber where it contacts with the leanest gas. Cool unstabilized naphtha is supplied at a lower section 28 of the absorber. One or more external cooler(s) 41 at suitable location along the absorber is used to remove heat of absorption from the absorber oil. External coolers return the absorber oil at about 30° C. to 40° C. to the absorber.

The process for recovering gaseous products from the product mixture obtained by contacting a hydrocarbon feed with a catalyst in a FCC process disclosed in prior art is shown in FIG. 2. FIG. 2 shows a fractionator (1) which contains gaseous mixture which is supplied to overhead cooler-condenser (3) via gas conduit. The entire or a part of the liquid fraction obtained from main fractionator overhead separator (5) is fed to an additional column referred to as unstabilized naphtha stripper (36) via conduit (7). This naphtha stripper reboils off lighter components from unstabilized naphtha to obtain a bottom liquid fraction having initial boiling point of between from about 25° C. to about 45° C. This liquid fraction or stripped naphtha, after being cooled in heat exchanger (39) at a temperature between about 20° C. to about 30° C., is supplied to absorber section (28) via conduit (38). The lighter gaseous fraction obtained from naphtha stripper (36) is recycled back to main fractionator cooler-condenser (3) via conduit (37).

The gaseous fraction is led through conduit (6) to suction of the first stage compressor (8), the discharge stream after getting cooled in inter-stage cooler (10) is separated into gas and liquid fractions in inter-stage receiver (11). This inter-stage liquid fraction, is combined in conduit (15) via conduit (13) with the gaseous fraction compressed in second stage. The stream in conduit (15) is further joined by rich oil stream from absorber bottom section (29) via conduit (30) and the overhead gaseous fraction from stripper (21) via conduit (20). The resultant stream is cooled in high pressure cooler (16) and thereafter separated into gas and liquid fractions in high pressure receiver cum separator (17).

The process for recovering gaseous products from the product mixture obtained by contacting a hydrocarbon feed with a catalyst in a FCC process disclosed in the present invention is shown in FIG. 3. FIG. 3 illustrates the process of the present invention wherein the entire or a part of the liquid fraction obtained from main fractionator overhead separator 5 is fed to High Pressure receiver 17 via conduit 7. The liquid from High pressure is fed to Deethanizer column 21 via conduit 19. The meanings of other notations are same as in FIG. 1. Higher amounts of debutanized naphtha are supplied to Primary absorber 27 via conduit 25 to absorb higher amount of Propylene and LPG.

Propylene and other gaseous components get absorbed in the liquid fraction during the process of condensing main fractionator overheads and remain absorbed in the liquid fraction even after separating the gas and liquid fractions. The obtained liquid fraction is also referred to as unstabilized naphtha. The absorption capacity of the unstabilized naphtha is much lower due to the presence of propylene and other gaseous component in it as compared to naphtha from debutanized bottoms (debutanized naphtha). Higher amounts of propylene and LPG can be absorbed by replacing the unstabilized naphtha with much lower flows of debutanized naphtha in the new modified process. Thus significant improvement in propylene recovery can be achieved by the use of the present invention wherein large amount of $C_3$-$C_4$ components are present in the unstabilized naphtha, this being the case for units where main column overhead receiver is operated at pressures of about 25 psig and above. The main advantage of the present invention is that it improves propylene and LPG from FCC fuel gas by effectively utilizing the additional capacities of Primary Absorber, $C_2$ stripper and debutanizer columns without loading Wet Gas compressor capacity.

The present invention provides an improved process for the recovery of propylene and LPG from a product mixture obtained by contacting a hydrocarbon feed with a catalyst in a FCC process, wherein the recovery is achieved by (i) distilling the product mixture in main fractionator to obtain a gaseous top product consisting of components boiling below 215° C.; (ii) cooling and condensing the gaseous top product and separating the obtained gas-liquid mixture in a receiver cum separator to obtain a liquid fraction or unstabilized naphtha and a lighter gaseous fraction; (iii) sequentially compressing, cooling and separating in a two stage Wet Gas compressor train said gaseous fraction obtained from step (ii) to obtain gaseous and liquid fractions from a high pressure separator; (iv) mixing the liquid fraction as obtained in step (ii) with the liquid fraction as obtained in step (iii) under high pressure separator to obtain combined liquid fraction; (v) feeding the combined liquid fraction as obtained in step (iv) to a de-ethanizer column wherein ethane and lighter components stripped off from the feed are recycled back to high pressure receiver in step (iii) whereas the de-ethanized liquid product is fed to debutanizer column; (vi) separating butane and lighter components present in the debutanizer feed as overhead gaseous fraction and obtaining heavier fraction as bottom product referred to as debutanizer bottoms; (vii) contacting gaseous fraction obtained from high pressure separator in step (iii) in an absorber with a part of the debutanizer bottoms viz., a part of the liquid fraction as obtained in step (vi); (viii) feeding the rich oil from the absorber bottom to de-ethanizer via high pressure receiver; (ix) optionally further treating the gaseous fraction from the absorber before leaving the FCC gas concentration section as fuel gas; characterized by feeding the entire or a part of unstabilized naphtha as obtained in step (ii), to the de-ethanizer via high pressure receiver and contacting the a part of debutanizer naphtha as obtained in step (vi) with the gaseous fractions obtained from high pressure separator in step (iii) in an absorber. In the present invention the main fractionator overhead condenser pressure is from 10 psig and above, preferably 25 psig and above. Besides this, the debutanized naphtha is supplied to the absorber at temperature preferably between from about 20° C. to about 30° C. using chilled water as an indirect cooling media whereby recovery of propylene and other $C_3$-$C_4$ components is further improved. In the process of the present invention the debutanizer bottoms recycle is supplied to absorber at about 20° C. to 30° C. by using chilled water/cooling water as cooling media in cooling exchangers.

It is to be understood that the structure of the present invention is susceptible to modifications, changes and adaptations by those skilled in the art. Such modifications, changes and adaptations are intended to be within the scope of the present invention which is further set forth under the following claims.

The present invention is illustrated and supported by the following examples. These are merely representative examples and optimization details and are not intended to restrict the scope of the present invention in any manner.

EXAMPLE

A simulation study comparing the various processes with the process of the present invention for achieving improvement in propylene recovery beyond 97% in terms of energy and total tray area.

Base case corresponds to the existing gas concentration unit as described above for which further increase in recoveries of propylene and LPG is possible by the following three process flow modifications:

Case 1: Conventional process-1: Providing additional capacity and reboiler duties in the absorber, de-ethanizer and debutanizer to accommodate increased gas-liquid flow in the loop for increasing recycle flow of Debutanizer naphtha (along with entire unsaturated naphtha flow) to the Primary Absorber.

Case 2: Conventional process-2: Providing additional column with required reboiler duty to generate additional stabilized naphtha by stripping off the lighters from unstabilized naphtha and supplying the stabilized naphtha to Primary Absorber (along with the Debutanizer Naphtha).

Case 3: Process of present invention: Withdrawing, in part or full, the flow of unsaturated naphtha from Primary Absorber; processing it sequentially in De-ethanizer and Debutanizer and increasing recycle of the Debutanizer naphtha to Primary Absorber. Additional capacity and Reboiler duties in the absorber, de-ethanizer and debutanizer are required to accommodate increased gas-liquid flow in the loop due to increased recycle flows, though no additional column for fractionation is required.

For all cases the temperature of the first absorber oil—unstabilized naphtha (in base case) and stripped naphtha (in present invention), is kept same at 320° C. to exclude the effect of cooling of absorber oil on propylene recovery. Improvement in recovery is expressed as reduction in propylene content of untreated fuel gas. Saturation level of the lean oil supplied to the absorber is expressed as mole fraction of propylene and other $C_3$-$C_4$ components present in it. For all cases, Energy efficiency is measured in terms of total of Reboiler duties for $C_2$ Stripper, Debutanizer and new unsaturated Naphtha stripper column plus wet gas compression duty; Capital expenditure is expressed as total tray X-sectional area for Primary Absorber, $C_2$ Stripper, Debutanizer and new unsaturated naphtha stripper column.

In case 1, for reducing the propylene in fuel gas from 3 mol % (base case) to 0.5 mol % and LPG from 4.3 mol % to 1.0 mol %, required recycle flow of Debutanizer naphtha to the Primary absorber to more than three times of the flow in base case with no change in unstabilized naphtha flow as seen in Table 1. Increasing the recycle of Debutanized naphtha by three, results in much larger liquid (also vapor) loads, and Reboiler duties as shown in Table 1. Liquid loads in Primary Absorber, $C_2$ Stripper and Debutanizer increases by about 73, 43 and 45% respectively over the base case. Also Reboiler duties required in C2 Stripper and Debutanizer are higher by about 67 and 40% respectively in case 3 over base case. The new design/revamp should provide for about 56%, 64% and 57% more tray x-sectional area for Primary Absorber, $C_2$ Stripper and Debutanizer column as compared to those in the base case. Overall, case 1 requires 44% more energy and 53% additional tray X-sectional area over base case for achieving same improvement in Propylene and LPG recovery over the base case.

In case 2 of Table 1, the same improvement in propylene and LPG recovery from fuel gas is achieved by stripping off lighters from unstabilized naphtha. Stripping lowers the total $C_3$ and $C_4$ content of the unstabilized naphtha from 24.6. mol % to 13.7 mol % and makes the absorber oil (stripped naphtha) leaner. The liquid load and reboiler duties for C2 Stripper and Debutanizer in this process (Case 2) remain same as in base case. The liquid load in primary absorber reduces by 7% in case 2 as compared to the base case. But 10% additional capacity is required for wet gas compressor. Overall, the Energy demand for the new design/revamp case using this process configuration is higher by just about 12% over the base case; 90% of this increased energy demand is used by the Reboiler for the new unsaturated Naphtha Stripper column, the remaining 10% is for compressing the lighter vapors stripped off the unsaturated Naphtha. Also, additional Capex for a new column of size equivalent to about 5% of the total Tray area of the Primary Absorber, $C_2$ Stripper and Debutanizer loop is required in this process configuration).

In the process of the present invention (Case 3) the same improvement in propylene and LPG recovery over the base case is achieved, without loading the wet gas compressor, by about doubling the recycle flow of Debutanized naphtha to the primary absorber and completely withdrawing the flow of unstabilized naphtha from the primary absorber; as seen by comparing case 1 and Case 3 in Table 1. This increases liquid loads in Primary Absorber, $C_2$ Stripper and Debutanizer by only about 31, 22 and 26% respectively over the base case. Reboiler duties required in $C_2$ Stripper and Debutanizer are higher by about 31 and 24% respectively in case 2 over base case. The new design/revamp should provide about 25% more tray cross-sectional area for each of $C_2$ Stripper and Debutanizer column as compared to those in the base case. But the increase in energy requirement, tray area over the base case are much lower than increase in the case 1 for achieving same improvement in propylene recovery.

With capacity and/or Reboiler duty limitations in the Primary Absorber-$C_2$ stripper-Debutanizer loop the process configuration in Case 2 is efficient out of various possible processes for achieving enhanced propylene and LPG recovery but requires additional column for fractionation. For a wet gas compressor limited cases (Case 1 and 3), the process of the present invention (case 3) is most energy and capital efficient for achieving same propylene recovery. No additional column for fractionation and additional wet gas compression capacity is required for either of case 1 and 3.

TABLE 1

Energy and Capex requirement for three process configurations studied for new design/revamp for achieving similar improvement in propylene and LPG recovery in FCC gas concentration unit.

|  | Base Case | Case 1 | Case 2 | Case 3 |
|---|---|---|---|---|
| Propylene in fuel gas, mol % | 3.0 | 0.5 | 0.5 | 0.5 |
| $C_3 + C_4$ in untreated fuel gas (mol %) | 4.3 | 1.0 | 1.1 | 1.0 |
| Propylene in Unsat Naphtha or $1^{st}$ absorber oil (mol %) | 5.2 | 5.2 | 0.15 | 5.2 |
| $C_3 + C_4$ in Unsat Naphtha or $1^{st}$ absorber oil (mol %) | 24.6 | 24.6 | 13.7 | 24.6 |
| Liquid Loads (T/hr) |  |  |  |  |
| Unsaturated naphtha | M1 | M1 | 0.0 | 0 |
| Stripped naphtha | 0.0 | 0.0 | 0.89 M1 | 0 |
| Debut bottom recycle | M2 | 3.24 M2 | M2 | 2.16 M2 |
| Total Liquid feed to Absorber Load | M3 (=M1 + M2) | 1.73 M3 | 0.93 M3 | 1.31 M3 |
| Feed to $C_2$ stripper | M4 | 1.43 M4 | M4 | 1.22 M4 |
| Feed to Debutanizer | M5 | 1.45 M5 | M5 | 1.26 M5 |
| Energy Inputs (GcaL/hr) |  |  |  |  |
| New Stripper Reboiler | 0.0 | 0.0 | Q1 | 0 |
| C2 Stripper Reboiler | Q2 | 1.67 Q2 | Q2 | 1.31 Q2 |
| Debut Reboiler | Q3 | 1.4 Q3 | Q3 | 1.24 Q3 |
| Wet Gas compression | Q4 | Q4 | 1.10 Q4 | Q4 |
| Total Energy required (Q1 + Q2 + Q3 + Q4) | Q | 1.44 Q | 1.12 Q | 1.23 Q |
| Total tray X-section Area |  |  |  |  |
| Primary Absorber | A1 | 1.56 A1 | A1 | A1 |
| C2 Stripper | A2 | 1.64 A2 | A2 | 1.25 A2 |
| Debutanizer | A3 | 1.57 A3 | A3 | 1.24 A3 |
| Naphtha Stripper (additional) | 0 | 0 | A4 | 0 |
| Total X-sec area (A1 + A2 + A3 + A4) | A | 1.53 A | 1.05 A | 1.20 A |

Base case: Unsaturated and Debutanized naphtha to Primary Absorber (PA)
Case 1: Unsaturated naphtha and increased Debutanized naphtha to PA
Case 2: Stripped Naphtha and Debutanized naphtha to PA
Case 3: Only Debutanized naphtha to PA (No flow/reduced flow of unstabilized naphtha to PA.)

The Main Advantages of the Present Invention are:
1. The present invention provides an energy efficient process for revamping/designing a unit limited by wet gas compressor capacity for enhancing the recovery of propylene and C4s from a product mixture obtained by contacting a hydrocarbon feed with a catalyst in a FCC process.
2. The process of the present invention improves propylene and LPG from FCC fuel gas by effectively utilizing the additional capacities of primary absorber, $C_2$ stripper and debutanizer columns without loading wet gas compressor capacity.
3. The process of the present invention helps in keeping sulfide levels lower in propylene by not cooling the unstabilized naphtha to deep sub-ambient temperatures.

We claim:
1. A process for the recovery of propylene and LPG from a product mixture obtained by contacting a hydrocarbon feed with a catalyst in a FCC process, comprising the steps:
   (i) distilling the product mixture in main fractionator to obtain heavier liquid product as side or bottom draws and a gaseous top product consisting of components boiling below 215° C.;
   (ii) cooling and condensing the gaseous top product and separating obtained gas-liquid mixture in a receiver cum separator to obtain a liquid fraction referred to as unstabilized naphtha and a lighter gaseous fraction;
   (iii) sequentially compressing, cooling and separating in a two stage wet gas compressor train said lighter gaseous fraction obtained from step (ii) to obtain gaseous fraction and liquid fraction from a high pressure separator;
   (iv) mixing the liquid fraction as obtained from step (ii) with the liquid fraction as obtained from step (iii) in the high pressure separator to obtain combined liquid fraction;
   (v) feeding the combined liquid fraction as obtained in step (iv) to a de-ethanizer to produce ethane and lighter components and a de-ethanized liquid product, wherein the ethane and lighter components are recycled back to the high pressure separator in step (iii) whereas the de-ethanized liquid product is fed to a debutanizer column;
   (vi) separating butane and lighter components from the de-ethanized liquid product as overhead gaseous frac- tion and obtaining heavier fraction as bottom product referred to as debutanizer bottoms in the debutanizer column;

(vii) contacting the gaseous fraction obtained from the high pressure separator in step (iii) in an absorber with a part of the debutanizer bottoms as obtained in step (vi) to produce a rich oil and a gaseous fraction; and (viii) feeding the rich oil from the absorber to the de-ethanizer via the high pressure separator, wherein the process is characterized by feeding at least or a part of the unstabilized naphtha as obtained in step (ii) to the de-ethanizer via the high pressure separator and contacting a part of the debutanizer bottoms as obtained in step (vi) with the gaseous fraction obtained from the high pressure separator in step (iii) in the absorber, wherein the at least part of the unstabilized naphtha obtained in step (ii) is fed directly to the high pressure separator and then sequentially to the de-ethanizer, the debutanizer column and the absorber without butane and lighter components being first stripped off from the unstabilized naphtha in a separate column and recycled whereby to avoid a need for compression of the recycled lighter components.

2. The process as claimed in claim 1, wherein an overhead condenser pressure in the main fractionator is from 10 prig and above.

3. The process as claimed in claim 1, wherein the debutanizer bottoms are supplied to the absorber at temperature from about 20° C. to about 30° C., wherein the temperature is adjusted by using chilled water as an indirect cooling media.

4. The process as claimed in claim 1, wherein the gaseous fraction from the absorber as obtained in step (vii) is further treated to recover gasoline range material.

5. The process as claimed in claim 2, wherein the debutanizer bottoms are supplied to the absorber at temperature from about 20° C. to about 30° C., wherein the temperature is adjusted by using chilled water as an indirect cooling media.

6. The process as claimed in claim 2, wherein the gaseous fraction from the absorber as obtained in step (vii) is further treated to recover gasoline range material.

7. The process as claimed in claim 3, wherein the gaseous fraction from the absorber as obtained in step (vii) is further treated to recover gasoline range material.

8. The process as claimed in claim 1, wherein an overhead condenser pressure in the main fractionator is from 25 psig and above.

9. The process as claimed in claim 1, wherein all of the unstabilized naphtha as obtained in step (ii) is fed directly to the high pressure separator, without butane and lighter components being first stripped off from the unstabilized naphtha in a separate column and recycled, and is then de-ethanized and debutanized before being passed to the absorber.

10. The process as claimed in claim 1, wherein the process consists essentially of the recited steps.

* * * * *